(12) United States Patent
Pacetti

(10) Patent No.: US 7,766,884 B2
(45) Date of Patent: Aug. 3, 2010

(54) POLYMERS OF FLUORINATED MONOMERS AND HYDROPHILIC MONOMERS

(75) Inventor: Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 677 days.

(21) Appl. No.: 11/807,091

(22) Filed: May 25, 2007

(65) Prior Publication Data

US 2007/0228345 A1 Oct. 4, 2007

Related U.S. Application Data

(62) Division of application No. 10/931,927, filed on Aug. 31, 2004, now Pat. No. 7,244,443.

(51) Int. Cl.
*A61M 5/32* (2006.01)

(52) U.S. Cl. ........................ 604/265; 424/423; 524/520; 524/544

(58) Field of Classification Search ................. 604/265; 424/423; 524/520, 544
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 2,968,649 A | 1/1961 | Pailthorp et al. |
| 3,051,677 A | 8/1962 | Rexford |
| 3,178,399 A | 4/1965 | Lo |
| 3,324,069 A | 6/1967 | Koblitz et al. |
| 3,773,737 A | 11/1973 | Goodman et al. |
| 3,779,805 A | 12/1973 | Alsberg |
| 3,849,514 A | 11/1974 | Gray, Jr. et al. |
| 3,856,827 A | 12/1974 | Cavitt |
| 4,076,929 A | 2/1978 | Dohany |
| 4,197,380 A | 4/1980 | Chao et al. |
| 4,226,243 A | 10/1980 | Shalaby et al. |
| 4,304,010 A | 12/1981 | Mano |
| 4,329,383 A | 5/1982 | Joh |
| 4,343,931 A | 8/1982 | Barrows |
| 4,346,710 A | 8/1982 | Thanawalla et al. |
| 4,353,960 A | 10/1982 | Endo et al. |
| 4,399,264 A | 8/1983 | Squire |
| 4,413,359 A | 11/1983 | Akiyama et al. |
| 4,423,183 A | 12/1983 | Close |
| 4,485,250 A | 11/1984 | Squire |
| 4,529,792 A | 7/1985 | Barrows |
| 4,530,569 A | 7/1985 | Squire |
| 4,564,013 A | 1/1986 | Lilenfeld et al. |
| 4,569,978 A | 2/1986 | Barber |
| 4,611,051 A | 9/1986 | Hayes et al. |
| 4,632,842 A | 12/1986 | Karwoski et al. |
| 4,636,346 A | 1/1987 | Gold et al. |
| 4,656,242 A | 4/1987 | Swan et al. |
| 4,718,907 A | 1/1988 | Karwoski et al. |
| 4,733,665 A | 3/1988 | Palmaz |
| 4,749,585 A | 6/1988 | Greco et al. |
| 4,754,009 A | 6/1988 | Squire |
| 4,770,939 A | 9/1988 | Sietsess et al. |
| 4,800,882 A | 1/1989 | Gianturco |
| 4,871,357 A | 10/1989 | Hsu et al. |
| 4,876,109 A | 10/1989 | Mayer et al. |
| 4,882,168 A | 11/1989 | Casey et al. |
| 4,886,062 A | 12/1989 | Wiktor |
| 4,897,457 A | 1/1990 | Nakamura et al. |
| 4,908,404 A | 3/1990 | Benedict et al. |
| 4,910,276 A | 3/1990 | Nakamura et al. |
| 4,931,287 A | 6/1990 | Bae et al. |
| 4,935,477 A | 6/1990 | Squire |
| 4,941,870 A | 7/1990 | Okada et al. |
| 4,948,851 A | 8/1990 | Squire |
| 4,973,142 A | 11/1990 | Squire |
| 4,975,505 A | 12/1990 | Squire |
| 4,977,008 A | 12/1990 | Squire |
| 4,977,025 A | 12/1990 | Squire |
| 4,977,026 A | 12/1990 | Squire |
| 4,977,297 A | 12/1990 | Squire |
| 4,977,901 A | 12/1990 | Ofstead |
| 4,982,056 A | 1/1991 | Squire |
| 4,985,308 A | 1/1991 | Squire |
| 4,999,248 A | 3/1991 | Squire |
| 5,000,547 A | 3/1991 | Squire |

(Continued)

FOREIGN PATENT DOCUMENTS

DE 42 24 401 1/1994

(Continued)

OTHER PUBLICATIONS

U.S. Appl. No. 10/176,504, filed Jun. 21, 2002, Roorda et al.
U.S. Appl. No. 10/176,510, filed Jun. 21, 2002, Hossainy et al.
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/198,912, filed Jul. 19, 2002, Ding et al.
U.S. Appl. No. 10/320,899, filed Dec. 16, 2002, Shah et al.
U.S. Appl. No. 10/376,348, filed Feb. 26, 2003, Ding et al.
U.S. Appl. No. 10/428,691, filed May 1, 2003, Pacetti.
3M, *Specialty Fluids 3M™ Fluorinert™ Liquids, Typical Properties*, http://www.3m.com/market/industrial/fluids/fluoprop.html, printed Mar. 30, 2001, 3 pages.
Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

(Continued)

*Primary Examiner*—Peter D. Mulcahy
*Assistant Examiner*—Henry Hu
(74) *Attorney, Agent, or Firm*—Squire Sanders & Dempsey, L.L.P.

(57) ABSTRACT

A polymer blend that contains a polymer of fluorinated monomers and another biocompatible polymer. The polymer blend can form a coating on a medical device. The medical device can be used for treat, prevent or ameliorate a medical condition.

12 Claims, No Drawings

U.S. PATENT DOCUMENTS

| | | |
|---|---|---|
| 5,006,382 A | 4/1991 | Squire |
| 5,019,096 A | 5/1991 | Fox, Jr. et al. |
| 5,030,394 A | 7/1991 | Sietses et al. |
| 5,047,020 A | 9/1991 | Hsu |
| 5,051,114 A | 9/1991 | Nemser et al. |
| 5,051,978 A | 9/1991 | Mayer et al. |
| 5,053,048 A | 10/1991 | Pinchuk |
| 5,076,659 A | 12/1991 | Bekiarian et al. |
| 5,093,427 A | 3/1992 | Barber |
| 5,100,992 A | 3/1992 | Cohn et al. |
| 5,107,852 A | 4/1992 | Davidson et al. |
| 5,110,645 A | 5/1992 | Matsumoto et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,176,972 A | 1/1993 | Bloom et al. |
| 5,185,408 A | 2/1993 | Tang et al. |
| 5,219,980 A | 6/1993 | Swidler |
| 5,246,451 A | 9/1993 | Trescony et al. |
| 5,258,020 A | 11/1993 | Froix |
| 5,272,012 A | 12/1993 | Opolski |
| 5,276,121 A | 1/1994 | Resnick |
| 5,292,516 A | 3/1994 | Viegas et al. |
| 5,296,283 A | 3/1994 | Froggatt |
| 5,298,260 A | 3/1994 | Viegas et al. |
| 5,300,295 A | 4/1994 | Viegas et al. |
| 5,302,385 A | 4/1994 | Khan et al. |
| 5,306,501 A | 4/1994 | Viegas et al. |
| 5,306,786 A | 4/1994 | Moens et al. |
| 5,308,685 A | 5/1994 | Froggatt |
| 5,310,838 A | 5/1994 | Hung et al. |
| 5,324,889 A | 6/1994 | Resnick |
| 5,326,839 A | 7/1994 | Resnick |
| 5,328,471 A | 7/1994 | Slepian |
| 5,330,768 A | 7/1994 | Park et al. |
| 5,336,518 A | 8/1994 | Narayanan et al. |
| 5,338,608 A | 8/1994 | Resnick |
| 5,342,348 A | 8/1994 | Kaplan |
| 5,353,368 A | 10/1994 | Resnick |
| 5,354,910 A | 10/1994 | Hung et al. |
| 5,368,566 A | 11/1994 | Crocker |
| 5,380,299 A | 1/1995 | Fearnot et al. |
| 5,383,853 A | 1/1995 | Jung et al. |
| 5,383,928 A | 1/1995 | Scott et al. |
| 5,395,311 A | 3/1995 | Andrews |
| 5,403,341 A | 4/1995 | Solar |
| 5,408,020 A | 4/1995 | Hung et al. |
| 5,417,969 A | 5/1995 | Hsu et al. |
| 5,417,981 A | 5/1995 | Endo et al. |
| 5,443,458 A | 8/1995 | Eury |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,545,208 A | 8/1996 | Wolff et al. |
| 5,560,463 A | 10/1996 | Link et al. |
| 5,562,734 A | 10/1996 | King |
| 5,569,463 A | 10/1996 | Helmus et al. |
| 5,575,818 A | 11/1996 | Pinchuk |
| 5,578,073 A | 11/1996 | Haimovich et al. |
| 5,584,877 A | 12/1996 | Miyake et al. |
| 5,591,224 A | 1/1997 | Schwartz et al. |
| 5,604,283 A | 2/1997 | Wada et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,616,608 A | 4/1997 | Kinsella et al. |
| 5,624,411 A | 4/1997 | Tuch |
| 5,628,728 A | 5/1997 | Tachibana et al. |
| 5,628,730 A | 5/1997 | Shapland et al. |
| 5,632,771 A | 5/1997 | Boatman et al. |
| 5,632,776 A | 5/1997 | Kurumatani et al. |
| 5,632,840 A | 5/1997 | Campbell |
| 5,635,201 A | 6/1997 | Fabo |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,684,061 A | 11/1997 | Ohnishi et al. |
| 5,691,311 A | 11/1997 | Maraganore et al. |
| 5,697,967 A | 12/1997 | Dinh et al. |
| 5,700,286 A | 12/1997 | Tartaglia et al. |
| 5,702,754 A | 12/1997 | Zhong |
| 5,711,958 A | 1/1998 | Cohn et al. |
| 5,713,949 A | 2/1998 | Jayaraman |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,750,234 A | 5/1998 | Johnson et al. |
| 5,758,205 A | 5/1998 | Hara et al. |
| 5,759,205 A * | 6/1998 | Valentini ..................... 433/173 |
| 5,760,118 A | 6/1998 | Sinclair et al. |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,804,318 A | 9/1998 | Pinchuk et al. |
| 5,820,917 A | 10/1998 | Tuch |
| 5,821,343 A * | 10/1998 | Keogh ......................... 530/402 |
| 5,824,048 A | 10/1998 | Tuch |
| 5,824,049 A | 10/1998 | Ragheb et al. |
| 5,827,587 A | 10/1998 | Fukushi |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,858,990 A | 1/1999 | Walsh |
| 5,860,963 A | 1/1999 | Azam et al. |
| 5,861,168 A | 1/1999 | Cooke et al. |
| 5,865,814 A | 2/1999 | Tuch |
| 5,869,127 A | 2/1999 | Zhong |
| 5,873,904 A | 2/1999 | Ragheb et al. |
| 5,874,165 A | 2/1999 | Drumheller |
| 5,876,433 A | 3/1999 | Lunn |
| 5,877,224 A | 3/1999 | Brocchini et al. |
| 5,879,697 A | 3/1999 | Ding et al. |
| 5,879,713 A | 3/1999 | Roth et al. |
| 5,897,911 A | 4/1999 | Loeffler |
| 5,900,425 A | 5/1999 | Kanikanti et al. |
| 5,902,875 A | 5/1999 | Roby et al. |
| 5,905,168 A | 5/1999 | Dos Santos et al. |
| 5,910,564 A | 6/1999 | Gruning et al. |
| 5,911,704 A | 6/1999 | Humes |
| 5,914,387 A | 6/1999 | Roby et al. |
| 5,919,893 A | 7/1999 | Roby et al. |
| 5,921,933 A | 7/1999 | Sarkis et al. |
| 5,922,393 A | 7/1999 | Jayaraman |
| 5,925,720 A | 7/1999 | Kataoka et al. |
| 5,928,279 A | 7/1999 | Shannon et al. |
| 5,932,299 A | 8/1999 | Katoot |
| 5,945,115 A | 8/1999 | Dunn et al. |

| | | | | | | |
|---|---|---|---|---|---|---|
| 5,955,509 | A | 9/1999 | Webber et al. | 6,306,176 B1 | 10/2001 | Whitbourne |
| 5,958,385 | A | 9/1999 | Tondeur et al. | 6,331,313 B1 | 12/2001 | Wong et al. |
| 5,962,138 | A | 10/1999 | Kolluri et al. | 6,335,029 B1 * | 1/2002 | Kamath et al. ............... 424/423 |
| 5,971,954 | A | 10/1999 | Conway et al. | 6,344,035 B1 | 2/2002 | Chudzik et al. |
| 5,980,928 | A | 11/1999 | Terry | 6,346,110 B2 | 2/2002 | Wu |
| 5,980,972 | A | 11/1999 | Ding | 6,358,556 B1 | 3/2002 | Ding et al. |
| 5,997,517 | A | 12/1999 | Whitbourne | 6,362,271 B1 | 3/2002 | Lin et al. |
| 6,010,530 | A | 1/2000 | Goicoechea | 6,379,381 B1 | 4/2002 | Hossainy et al. |
| 6,011,125 | A | 1/2000 | Lohmeijer et al. | 6,387,379 B1 | 5/2002 | Goldberg et al. |
| 6,015,541 | A | 1/2000 | Greff et al. | 6,395,326 B1 | 5/2002 | Castro et al. |
| 6,033,582 | A | 3/2000 | Lee et al. | 6,408,878 B2 | 6/2002 | Unger et al. |
| 6,033,724 | A | 3/2000 | Molitor | 6,410,612 B1 | 6/2002 | Hatanaka |
| 6,034,204 | A | 3/2000 | Mohr et al. | 6,419,692 B1 | 7/2002 | Yang et al. |
| 6,042,875 | A | 3/2000 | Ding et al. | 6,451,373 B1 | 9/2002 | Hossainy et al. |
| 6,051,576 | A | 4/2000 | Ashton et al. | 6,464,683 B1 | 10/2002 | Samuelson et al. |
| 6,051,648 | A | 4/2000 | Rhee et al. | 6,482,834 B2 | 11/2002 | Spada et al. |
| 6,054,553 | A | 4/2000 | Groth et al. | 6,494,862 B1 | 12/2002 | Ray et al. |
| 6,056,993 | A | 5/2000 | Leidner et al. | 6,503,538 B1 | 1/2003 | Chu et al. |
| 6,060,451 | A | 5/2000 | DiMaio et al. | 6,503,556 B2 | 1/2003 | Harish et al. |
| 6,060,518 | A | 5/2000 | Kabanov et al. | 6,503,954 B1 | 1/2003 | Bhat et al. |
| 6,060,534 | A | 5/2000 | Ronan et al. | 6,506,437 B1 | 1/2003 | Harish et al. |
| 6,080,488 | A | 6/2000 | Hostettler et al. | 6,524,347 B1 | 2/2003 | Myers et al. |
| 6,090,134 | A | 7/2000 | Tu et al. | 6,527,801 B1 | 3/2003 | Dutta |
| 6,096,070 | A | 8/2000 | Ragheb et al. | 6,527,863 B1 | 3/2003 | Pacetti et al. |
| 6,096,396 | A | 8/2000 | Patton et al. | 6,528,526 B1 | 3/2003 | Myers et al. |
| 6,096,798 | A | 8/2000 | Luthra et al. | 6,530,950 B1 | 3/2003 | Alvarado et al. |
| 6,096,809 | A | 8/2000 | Lorcks et al. | 6,530,951 B1 | 3/2003 | Bates et al. |
| 6,099,562 | A | 8/2000 | Ding et al. | 6,540,776 B2 | 4/2003 | Sanders Millare et al. |
| 6,099,563 | A | 8/2000 | Zhong | 6,544,223 B1 | 4/2003 | Kokish |
| 6,110,188 | A | 8/2000 | Narciso, Jr. | 6,544,543 B1 | 4/2003 | Mandrusov et al. |
| 6,110,483 | A | 8/2000 | Whitbourne et al. | 6,544,582 B1 | 4/2003 | Yoe |
| 6,113,629 | A | 9/2000 | Ken | 6,545,097 B2 | 4/2003 | Pinchuk et al. |
| 6,120,491 | A | 9/2000 | Kohn et al. | 6,551,708 B2 | 4/2003 | Tsuda et al. |
| 6,120,536 | A | 9/2000 | Ding et al. | 6,555,157 B1 | 4/2003 | Hossainy |
| 6,120,788 | A | 9/2000 | Barrows | 6,558,733 B1 | 5/2003 | Hossainy et al. |
| 6,120,904 | A | 9/2000 | Hostettler et al. | 6,565,659 B1 | 5/2003 | Pacetti et al. |
| 6,121,027 | A | 9/2000 | Clapper et al. | 6,572,644 B1 | 6/2003 | Moein |
| 6,124,045 | A | 9/2000 | Soda et al. | 6,585,755 B2 | 7/2003 | Jackson et al. |
| 6,129,761 | A | 10/2000 | Hubbell | 6,585,765 B1 | 7/2003 | Hossainy et al. |
| 6,136,333 | A | 10/2000 | Cohn et al. | 6,585,926 B1 | 7/2003 | Mirzaee |
| 6,143,354 | A | 11/2000 | Koulik et al. | 6,605,154 B1 | 8/2003 | Villareal |
| 6,153,252 | A | 11/2000 | Hossainy et al. | 6,616,765 B1 | 9/2003 | Hossaony et al. |
| 6,159,978 | A | 12/2000 | Myers et al. | 6,623,448 B2 | 9/2003 | Slater |
| 6,165,212 | A | 12/2000 | Dereume et al. | 6,625,486 B2 | 9/2003 | Lundkvist et al. |
| 6,172,167 | B1 | 1/2001 | Stapert et al. | 6,645,135 B1 | 11/2003 | Bhat |
| 6,177,523 | B1 | 1/2001 | Reich et al. | 6,645,195 B1 | 11/2003 | Bhat et al. |
| 6,179,817 | B1 | 1/2001 | Zhong | 6,656,216 B1 | 12/2003 | Hossainy et al. |
| 6,180,632 | B1 | 1/2001 | Myers et al. | 6,656,506 B1 | 12/2003 | Wu et al. |
| 6,197,051 | B1 | 3/2001 | Zhong | 6,660,034 B1 | 12/2003 | Mandrusov et al. |
| 6,203,551 | B1 | 3/2001 | Wu | 6,663,662 B2 | 12/2003 | Pacetti et al. |
| 6,211,249 | B1 | 4/2001 | Cohn et al. | 6,663,880 B1 | 12/2003 | Roorda et al. |
| 6,214,901 | B1 | 4/2001 | Chudzik et al. | 6,666,880 B1 | 12/2003 | Chiu et al. |
| 6,224,894 | B1 | 5/2001 | Jamiolkowski et al. | 6,673,154 B1 | 1/2004 | Pacetti et al. |
| 6,231,590 | B1 | 5/2001 | Slaikeu et al. | 6,673,385 B1 | 1/2004 | Ding et al. |
| 6,231,600 | B1 | 5/2001 | Zhong | 6,689,099 B2 | 2/2004 | Mirzaee |
| 6,240,616 | B1 | 6/2001 | Yan | 6,695,920 B1 | 2/2004 | Pacetti et al. |
| 6,242,041 | B1 | 6/2001 | Katoot et al. | 6,706,013 B1 | 3/2004 | Bhat et al. |
| 6,245,753 | B1 | 6/2001 | Byun et al. | 6,709,514 B1 | 3/2004 | Hossainy |
| 6,245,760 | B1 | 6/2001 | He et al. | 6,712,845 B2 | 3/2004 | Hossainy |
| 6,248,129 | B1 | 6/2001 | Froix | 6,713,119 B2 | 3/2004 | Hossainy et al. |
| 6,251,136 | B1 | 6/2001 | Guruwaiya et al. | 6,716,444 B1 | 4/2004 | Castro et al. |
| 6,254,632 | B1 | 7/2001 | Wu et al. | 6,723,120 B2 | 4/2004 | Yan |
| 6,258,121 | B1 | 7/2001 | Yang et al. | 6,733,768 B2 | 5/2004 | Hossainy et al. |
| 6,258,371 | B1 | 7/2001 | Koulik et al. | 6,740,040 B1 | 5/2004 | Mandrusov et al. |
| 6,262,034 | B1 | 7/2001 | Mathiowitz et al. | 6,743,462 B1 | 6/2004 | Pacetti |
| 6,270,788 | B1 | 8/2001 | Koulik et al. | 6,746,773 B2 | 6/2004 | Llanos et al. |
| 6,273,913 | B1 | 8/2001 | Wright et al. | 6,749,626 B1 | 6/2004 | Bhat et al. |
| 6,277,449 | B1 | 8/2001 | Kolluri et al. | 6,753,071 B1 | 6/2004 | Pacetti et al. |
| 6,283,947 | B1 | 9/2001 | Mirzaee | 6,758,859 B1 | 7/2004 | Dang et al. |
| 6,283,949 | B1 | 9/2001 | Roorda | 6,759,054 B2 | 7/2004 | Chen et al. |
| 6,284,305 | B1 | 9/2001 | Ding et al. | 6,764,505 B1 | 7/2004 | Hossainy et al. |
| 6,287,628 | B1 | 9/2001 | Hossainy et al. | 6,926,919 B1 * | 8/2005 | Hossainy et al. ............ 427/2.25 |
| 6,299,604 | B1 * | 10/2001 | Ragheb et al. ............... 604/265 | 7,008,979 B2 * | 3/2006 | Schottman et al. ........... 523/334 |

| | | |
|---|---|---|
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0090389 A1 | 7/2002 | Humes et al. |
| 2002/0091433 A1 | 7/2002 | Ding et al. |
| 2002/0094440 A1 | 7/2002 | Llanos et al. |
| 2002/0099438 A1 | 7/2002 | Furst |
| 2002/0111590 A1 | 8/2002 | Davila et al. |
| 2002/0120326 A1 | 8/2002 | Michal |
| 2002/0122877 A1 | 9/2002 | Harish et al. |
| 2002/0123801 A1 | 9/2002 | Pacetti et al. |
| 2002/0133183 A1 | 9/2002 | Lentz et al. |
| 2002/0142039 A1 | 10/2002 | Claude |
| 2002/0143386 A1 | 10/2002 | Davila et al. |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0004563 A1 | 1/2003 | Jackson et al. |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065346 A1 | 4/2003 | Evens et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0077312 A1 | 4/2003 | Schmulewicz et al. |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0102758 A1 | 5/2004 | Davila et al. |

FOREIGN PATENT DOCUMENTS

| | | |
|---|---|---|
| DE | 19723723 | 12/1998 |
| EP | 0 301 856 | 2/1989 |
| EP | 0 362 858 | 4/1990 |
| EP | 0 396 429 | 11/1990 |
| EP | 0 398 250 | 11/1990 |
| EP | 0 514 406 | 11/1992 |
| EP | 0 568310 1 | 11/1993 |
| EP | 0 604 022 | 6/1994 |
| EP | 0 623 354 | 11/1994 |
| EP | 0 633 032 | 1/1995 |
| EP | 0 665 023 | 8/1995 |
| EP | 0 701 802 | 3/1996 |
| EP | 0 716 836 | 6/1996 |
| EP | 0 747069 | 12/1996 |
| EP | 0 809 999 | 12/1997 |
| EP | 0 815803 | 1/1998 |
| EP | 0 832 655 | 4/1998 |
| EP | 0 850 651 | 7/1998 |
| EP | 0 879 595 | 11/1998 |
| EP | 0 893108 | 1/1999 |
| EP | 0 910 584 | 4/1999 |
| EP | 0 923 953 | 6/1999 |
| EP | 0 950385 | 10/1999 |
| EP | 0 950386 | 10/1999 |
| EP | 0 953 320 | 11/1999 |
| EP | 0 970 711 | 1/2000 |
| EP | 0 968688 | 1/2000 |
| EP | 0 982 041 | 3/2000 |
| EP | 0 997115 | 5/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 92/05695 | 4/1992 |
| WO | WO 92/18320 | 10/1992 |
| WO | WO 94/02185 | 2/1994 |
| WO | WO 94/09760 | 5/1994 |
| WO | WO 95/10989 | 4/1995 |
| WO | WO 95/24929 | 9/1995 |
| WO | WO 96/21404 | 7/1996 |
| WO | WO 96/40174 | 12/1996 |
| WO | WO 97/10011 | 3/1997 |
| WO | WO 97/41164 | 11/1997 |
| WO | WO 97/45105 | 12/1997 |
| WO | WO 97/46590 | 12/1997 |
| WO | WO 98/08463 | 3/1998 |
| WO | WO 98/13405 | 4/1998 |
| WO | WO 98/17331 | 4/1998 |
| WO | WO 98/32398 | 7/1998 |
| WO | WO 98/36784 | 8/1998 |

| | | |
|---|---|---|
| WO | WO 98/58680 | 12/1998 |
| WO | WO 99/01118 | 1/1999 |
| WO | WO 99/32051 | 7/1999 |
| WO | WO 99/38546 | 8/1999 |
| WO | WO 99/55396 | 11/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/27455 | 5/2000 |
| WO | WO 00/29043 | 5/2000 |
| WO | WO 00/32255 | 6/2000 |
| WO | WO 00/38754 | 7/2000 |
| WO | WO 00/41738 | 7/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/30403 | 5/2001 |
| WO | WO 01/45763 | 6/2001 |
| WO | WO 01/49338 | 7/2001 |
| WO | WO 01/49340 | 7/2001 |
| WO | WO 01/51027 | 7/2001 |
| WO | WO 01/74414 | 10/2001 |
| WO | WO 01/87342 | 11/2001 |
| WO | WO 01/87368 | 11/2001 |
| WO | WO 01/87372 | 11/2001 |
| WO | WO 01/87376 | 11/2001 |
| WO | WO 02/03890 | 1/2002 |
| WO | WO 02/24249 | 3/2002 |
| WO | WO 02/26139 | 4/2002 |
| WO | WO 02/26162 | 4/2002 |
| WO | WO 02/26271 | 4/2002 |
| WO | WO 02/26281 | 4/2002 |
| WO | WO 02/34311 | 5/2002 |
| WO | WO 02/47731 | 6/2002 |
| WO | WO 02/47732 | 6/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/022324 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2005/049678 | 6/2005 |
| WO | WO 2005/092406 | 10/2005 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Arnold et al., *Effects of environment on the creep properties of a poly (ethylmethacrylate) based bone cement* J. Mater. Sci: Mater. In Med., vol. 12, pp. 707-717 (2001).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Bellex International, *CYTOP ®*, http://www.bellexinternational.com/cytop.htm, printed Mar. 30, 2001, 1 page.

Bellex International, *CYTOP®, Amorphous Fluorocarbon Polymer*, 1 page (no date).

Bellex International, *Selected CYTOP Physical Data*, 1 page (no date).

Chung et al., *Inner core segment design for drug delivery control of thermo-responsive polymeric micelles*, Journal of Controlled Release 65:93-103 (2000).

Cífková et al., *Irritation effects of residual products derived from p(HEMA) gels*,Biomaterials, vol. 9, (Jul. 1998), pp. 372-375.

Dalsin et al., *DOPA: A New Anchor for PEGylation of Biomaterial Surfaces*, Soc. For Biomaterials 28$^{th}$ Annual Meeting Transactions, pp. 40 (2002).

Deb et al., *Effect of crosslinking agents on poly(ethylmethacrylate) bone cements*, J. of Mater.Sci: Mater. In Med., vol. 8, pp. 829-833 (1997).

Del Guerra et al., *In vitro biocompatibility of fluorinated polyurethanes*, J. Mater. Sci. In Med., vol. 5, pp. 452-456 (1994).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

DuPont, *Available Grades of DuPont Teflon® AF*, Teflon Amorphous Fluoropolymer, http://www.dupont.com/teflon/af/grades.html, printed Sep. 21, 2004, 2 pages.

DuPont, *High-Performance/Potential Applications*, Teflon Amorphous Fluoropolymer, http://www.dupont.com/teflon/af/potapps.html, printed Mar. 30, 2001, 3 pages.

DuPont, Sales Notice, Teflon Amorphous Fluoropolymer, http://www.dupont.com/teflon/af/patent.html, printed Sep. 21, 2004, 2 pages.

DuPont, *Teflon AF 1601S amorphous fluoropolymer solutions*, product information, 2 pages (1998).

DuPont, *Teflon® AF amorphous fluoropolymers*, Product Information, 6 pages (1998).

DuPont, *Teflon® AF: A New Generation of High-Performance Fluoropolymer Resins*, http://www.dupont.com/teflon/af/index.html, printed Mar. 30, 2001, 1 page.

DuPont, *Teflon® Protects Superconductors Against Acid*, Teflon Amorphous Fluoropolymer, http://www.dupont.com/teflon/af/superconductor.html, printed Sep. 21, 2004, 2 pages.

DuPont, *Unique Properties of Teflon® AF*, Teflon Amorphous Fluoropolymer, http://www.dupont.com/teflon/af/unique.html, printed Mar. 30, 2001, 3 pages.

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Fine et al., *Improved nerve regeneration through piezoelectric vinylidenefluoride- trifluoroethylene copolymer guidance channels*, Biomaterials, vol. 12, Oct., pp. 775-780 (1991).

Fischell, *Polymer Coatings for Stents*, Circulation, 94:1494-95 (1996).

Gullickson, *Reference Data Sheet on Common Chlorinated Solvents*, http://www.mcs.net/~hutter/tee/chlorina.html, printed Mar. 30, 2001, 5 pages.

Gunn et al., *Stent coatings and local drug delivery*, Eur. Heart J., vol. 20, issue 23, pp. 1693-1700 (1999).

Harper et al., *Fatigue Characteristics of Polyethylmethacrylate Based Bone Cement Reinforced with Silane Coupled Hydroxyapatite*, Fifth World Biomaterials Congress, May 29-Jun. 2, 1996, Toronto, Canada, Abstract 351, 3 pgs.

Harper et al., *Mechanical properties of hydroxyapatite reinforced poly (ethyl methacrylate) bone cement after immersion in a physiological solution: influence of a silane coupling agent*, J. Mater. Sci.: Mater. In Med., vol. 11, pp. 491-497 (2000).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

International Search Report for PCT appl. PCT/US03/15347, filed May 14, 2003, date of mailing Sep. 4, 2003, 6 pgs.

International Search Report for PCT appl. PCT/US03/15544, filed May 14, 2003, date of mailing Jan. 23, 2004, 9 pgs.

International Search Report for PCT appl. PCT/US03/21170, filed Jul. 2, 2003, date of mailing Oct. 31, 2003, 8 pgs.

International Search Report for PCT appl. PCT/US03/28643, filed Sep. 10, 2003, date of mailing Mar. 12, 2003, 10 pgs.

International Search Report for PCT/US2005/030586, mailed Jan. 17, 2006, 11 pgs.

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarboxylic Acids*, Journal of Polymer Science, Part A: Polymer Chemistry, 37(4), 391-407 (1999).

Kruft et al., *Studies on radio-opaque polymeric biomaterials with potential applications to endovascular prostheses*, Biomaterials, vol. 17, No. 18, pp. 1803-1812 (1996).

Lambert et al., *Localized Arterial Wall Drug Delivery From a Polymer-Coated Removable Metallic Stent*, Circulation, vol. 90, No. 2, pp. 1003-1011 (1994).

Laroche et al., *Polyvinylidene fluoride (PVDF) as a biomaterial: From polymeric raw material to monofilament vascular suture*, J. of Biomedical Mat. Research, vol. 29, pp. 1525-1536 (1995).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Lin et al., *Fluropolymer Alloys Performance Optimization of PVDF Alloys*, Fluropolymers 2 Properties, edited by Hougham et al., Plenum Publishers N.Y. pp. 121-136 (1999).

Lin et al., *Surface characterization and platelet adhesion studies on fluorocarbons prepared by plasma-induced graft polymerization*, J. Biomater Sci. Polymer Edn., vol. 11, No. 7, pp. 701-714 (2000).

Liu et al., *Drug release characteristics of unimolecular polymeric micelles*, Journal of Controlled Release 68:167-174 (2000).

Luthra, Biointeractions Ltd (BIL), http://www.biomateria.com/biointeractions.html, printed Sep. 21, 2004, 3 pages.

Marconi et al., *Covalent bonding of heparin to a vinyl copolymer for biomedical applications*, Biomaterials 18(12):885-890 (1997).

Materials Engineering, *Applications in Design/Manufacturing/R&D*, Materials Selector 1993, Penton Publishing (1992) 6 pgs.

Matsumaru et al., *Embolic Materials for Endovascular Treatment of Cerebral Lesions*, J. Biomater. Sci. Polymer Edn 8(7):555-569 (1997).

Medtronic, Trillium Affinity NT, Oxygenator, Product Information, 6 pages (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

NCMS SOLV-DB, *Query Results for: CFC*, http://solvdb.ncms.org/CAT01.idc?chemcat=CFC, printed Mar. 30, 2001, 2 pages.

NCMS SOLV-DB, *Query Results for: FC-75 Fluorinert*, http://solvdb.ncms.org/common01.idc, printed Mar. 30, 2001, 2 pages.

Nordrehaug et al., *A novel biocompatible coating applied to coronary stents*, European Heart Journal 14, p. 321 (P1694), Abstr. Suppl. (1993).

Novick et al., *Protein-containing hydrophobic coatings and films*, Biomaterials, vol. 23, No. 2 (2002) pp. 441-448.

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Parkell, Inc., *Material Safety Data Sheets*, http://www.parkell.com/msds.html, printed Oct. 21, 2004, 2 pgs.

Parkell, Inc., *MSDS No: S426, VAR, Material Safety Data Sheet*, 2 pgs (2002).

Parkell, Inc., MSDS No: S441, Material Safety Data Sheet, 2 pgs (2002).

Parkell, Inc., *SNAP Powder-Liquid Temporary Crown and Bridge Resin*, http://www.parkell.com/snap.html, printed Oct. 21, 2004, 1 pg.

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Porté-Durrieu et al., *Development of "Heparin-Like" Polymers Using Swift Heavy Ion and Gamma Radiation. I. Preparation and Characterization of the Materials*, Surface Treatment of Biomaterials, pp. 119-127 (2000).

Porté-Durrieu et al., *Surface Treatment of Biomaterials by Gamma and Swift Heavy Ions Grafting*, Nuclear Instruments and Methods in Physics Research, vol. B 151, pp. 404-415 (1999).

Revell et al., *Experimental Studies of the Biological Response to a New Bone Cement: II Soft Tissue Reactions in the Rat*, Clinical Materials, vol. 10, pp. 233-238 (1992).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

Techspray, Bulk Solvents, http://www.techspray.com/bulksup.htm, printed Sep. 21, 2004, 3 pages.

Techspray, *Flux Remover AMS*, Product Information, http://www.techspray.com/1665info.htm, printed Aug. 28, 2001, 2 pages.

Teomin et al., *Perivascular delivery of heparin for the reduction of smooth muscle cell proliferation after endothelial injury*, J. of Controlled Release, vol. 60, pp. 129-142 (1999).

Topol et al., *Frontiers in Interventional Cardiology*, Circulation, vol. 98, pp. 1802-1820 (1998).

Urban et al., *Why Make Monofilament Sutures Out of Polyvinylidene Fluoride?*, ASAIO J., vol. 40, No. 2, pp. 145-156 (1994).

Van Beusekom et al., *Coronary stent coatings*, Coronary Artery Disease 5(7):590-596 (Jul. 1994).

Verweire et al., *Evaluation of fluorinated polymers as coronary stent coating*, J. Mater.Sci: Mater. In Med., vol. 11, No. 4, pp. 207-212 (2000).

Weightman et al., *The Mechanical Properties of Cement and Loosening of the Femoral Component of Hip Replacements*, J. Bone and Joint Surg., vol. 69-B, No. 4, pp. 558-564 (Aug. 1987).

Wholey et al., *Global Experience in Cervical Carotid Artery Stent Placement*, Catherization and Cardiovascular Inteventions, vol. 50, No. 2, pp. 160-167 (2000).

Wilensky et al., *Methods and Devices for Local Drug Delivery in Coronary and Peripheral Arteries*, Trends Cardiovasc. Med. 3(5):163-170 (1993).

Woo et al., *Phase Behavior of Polycarbonate Blends with Selected Halogenated Polymers*, J. Appl. Polym. Sci., vol. 30, pp. 4243-4249 (1985).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

POLYMERS OF FLUORINATED MONOMERS AND HYDROPHILIC MONOMERS

This application is a divisional application of U.S. application Ser. No. 10/931,927, filed on Aug. 31, 2004, now U.S. Pat. No. 7,244,443 the teaching of which is incorporated herein in its entirety by reference.

BACKGROUND OF THE INVENTION

1. Field of the Invention

This invention generally relates to a polymeric material useful for coating an implantable device, such as a stent.

2. Description of the Background

Although stents work well mechanically, the chronic issues of restenosis and, to a lesser extent, stent thrombosis remain. Pharmacological therapy in the form of a drug-delivery stent appears a feasible means to tackle these biologically derived issues. Polymeric coatings placed onto the stent serve to act both as the drug reservoir, and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

The nature of the coating polymers plays an important role in defining the surface properties of a coating. For example, a very low $T_g$, amorphous coating material can have unacceptable rheological behavior upon mechanical perturbation such as crimping, balloon expansion, etc. On the other hand, a high $T_g$, or highly crystalline coating material introduces brittle fracture in the high strain areas of the stent pattern.

A current paradigm in biomaterials is the control of protein adsorption on the implant surface. Uncontrolled protein adsorption, leading to mixed layer of partially denatured proteins, is a hallmark of current biomaterials when implanted. Such a surface presents different cell binding sites from adsorbed plasma proteins such as fibrogen and immunoglobulin G. Platelets and inflammatory cells such as monocyte/macrophages and neutrophils adhere to these surfaces. Unfavorable events can be controlled by the use of non-fouling surfaces. These are materials, which absorb little or no protein, primarily due to their hydrophilic surface properties.

Another limitation of current drug-delivery stents stems from the fact that the stent is a foreign body. Use of drug-delivery stents has proved successful by use of controlled release of anti-proliferative or anti-inflammatory drugs to control restenosis. However, drug-delivery stents still have a small, but measurable, incidence of sub-acute thrombosis. Moreover, drug-delivery stents have not driven restenosis to zero levels, especially in more challenging patient subsets such as diabetics or patients with small vessels, and/or long, diffuse lesions. A biomaterials-based strategy for further improving the outcome of drug-delivery stents is by the use of biobeneficial materials or surfaces in stent coatings. A biobeneficial material is one which enhances the biocompatibility of a device by being non-fouling, hemocompatible, actively non-thrombogenic, or anti-inflammatory, all without depending on the release of a pharmaceutically active agent.

Some of the currently used polymeric materials such as poly(vinylidene-co-hexafluoropropene) have good mechanical properties, and acceptable biocompatibility, but also have low permeability to drugs. One proposed solution to ameliorate this issue is to blend in hydrophilic polymers. However, it is well known in the art that many hydrophilic materials such as polyethylene oxide or hyaluronic acid are water-soluble and can be leached out of the composition such that the coating may lose biobeneficiality. Such polymeric blends can also have compromised mechanical properties, particularly the ultimate elongation.

The present invention addresses such problems by providing a polymeric material for coating implantable devices.

SUMMARY OF THE INVENTION

Provided herein is a polymer formed of fluorinated monomers and hydrophilic monomers. The fluorinated monomers can provide mechanical strength and/or flexibility, biocompatibility, and physiologic durablity for the polymer. The hydrophilic monomers impart drug permeability to the polymer, and can provide additional biobeneficial properties.

In one embodiment, the polymer can be a random or block polymer having a general formula as shown below (Formula I):

Formula I where m and n can be 0 or positive integers ranging from, e.g., 1 to 100,000 and m+n≠0; and o can be a positive integer ranging from, e.g., 1 to 100,000.

The strength fluoro monomers are generally fluorinated ethylene monomers such as —$CF_2$—$CF_2$—, —$CH_2$—$CF_2$—, —$CH_2$—CHF—, —$CF_2$—CHF—, —CHF—CHF—, or $CF_2$—CRF— where R can be phenyl, cyclic alkyl, heterocyclic, heteroaryl, fluorinated phenyl, fluorinated cyclic alkyl, or fluorinated heterocyclic.

The flexibility fluoro monomers are generally substituted fluorinated ethylene monomers bearing a substituent (R), —$CF_2$—CRF—, —CHF—CRF—, and —$CF_2$—CRH—. R can be trifluoromethyl, F, Cl, Br, I, short chain alkyl groups from $C_2$ to $C_{12}$, fluorinated short chain alkyl groups from $C_2$ to $C_{12}$, and combinations thereof.

The hydrophilic monomers can be any vinyl monomer having pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) groups, poly(tetramethylene glycol) groups, poly(alkylene oxide), hydroxyl group(s), or a substituent that bears a charge and/or any of pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) group(s), poly(tetramethylene glycol) group(s), poly (alkylene oxide) group(s), and hydroxyl group(s). Some exemplary hydrophilic monomers are vinyl pyrrolidone, hydroxyethyl methacrylate, hydroxypropyl methacrylate, methyl vinyl ether, alkyl vinyl ether, vinyl alcohol, methacrylic acid, acrylic acid, acrylamide, N-alkyl acrylamide, hydroxypropylmethacrylamide, vinyl acetate, 2-sulfoethyl methacrylate, 3-sulfopropyl acrylate, 3-sulfopropyl methacrylate, and PEG-methacrylate. Some exemplary substituents bearing a charge can be, for example, choline, phosphoryl choline, 2-aminoethyl methacrylate hydrochloride, N-(3-aminopropyl)methacrylamide hydrochloride, 2-N-morpholinoethyl methacrylate, vinylbenzoic acid, vinyl sulfonic acid, and styrene sulfonates.

The monomers for strength generally account for about 60 mole % to about 90 mole % of the total monomers forming the polymer, the monomers for flexibility generally account for about 0 mole % to about 40 mole % of the total monomers forming the polymer, and the hydrophilic monomers for enhancing permeability generally account for about 0 mole % to about 20 mole % of the total monomers forming the polymer. By varying the mole percentages of the three components of the polymer, one can fine-tune physical properties of the polymer.

In another embodiment, it is provided a polymer blend that includes a polymer that has fluorinated monomers and at least one other biocompatible polymer. In one embodiment, the polymer that has fluorinated monomers has a structure of formula I as defined above.

The polymer or polymer blends described herein can be used to form a coating(s) on an implantable device. The polymers or polymer blends described herein can also be used to form the implantable device itself. The implantable device can optionally include a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudicationanastomotic proliferation for vein and artificial grafts, bile duct obstruction, ureter obstruction, tumor obstruction, or combinations thereof.

DETAILED DESCRIPTION

Polymers of Fluorinated Monomers and Hydrophilic Monomers

Provided herein is a polymer formed of fluorinated monomers and hydrophilic monomers. The fluorinated monomers can provide mechanical strength and/or flexibility, biocompatibility, and physiologic durablity for the polymer. The hydrophilic monomers impart drug permeability to the polymer, and can provide additional biobeneficial properties.

In one embodiment, the polymer can be a random or block polymer having a general formula as shown below (Formula I):

Formula I where m and n can be 0 or positive integers ranging from, e.g., 1 to 100,000 and m+n≠0; and o can be a positive integer ranging from, e.g., 1 to 100,000. The strength fluoro monomer can be in the range of, e.g., from about 60 mole % to about 90 mole %, the flexibility fluoro monomer can be in the range of, e.g., from about 0 mole % to about 40 mole %, and the hydrophilic monomer can be in the range from above 0 mole % to about 20 mole %.

The strength fluoro monomers are generally fluorinated ethylene monomers such as $-CF_2-CF_2-$, $-CH_2-CF_2-$, $-CH_2-CHF-$, $-CF_2-CHF-$, $-CHF-CHF-$, or $CF_2-CRF-$ where R can be phenyl, cyclic alkyl, heterocyclic, heteroaryl, fluorinated phenyl, fluorinated cyclic alkyl, or fluorinated heterocyclic.

The flexibility fluoro monomers are generally substituted fluorinated ethylene monomers bearing a substituent (R), $-CF_2-CRF-$, $-CHF-CRF-$, and $-CF_2-CRH-$. R can be trifluoromethyl, F, Cl, Br, I, short chain alkyl groups from $C_2$ to $C_{12}$, fluorinated short chain alkyl groups from $C_2$ to $C_{12}$, and combinations thereof.

The hydrophilic monomers can be any vinyl monomer having pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) group(s), poly(tetramethylene glycol) group(s), poly(alkylene oxide) group(s), hydroxyl group(s), or a substituent that bears a charge and/or any of pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) group(s), poly(tetramethylene glycol) group(s), poly(alkylene oxide) group(s), and hydroxyl group(s). Some exemplary hydrophilic monomers are vinyl pyrrolidone, hydroxyethyl methacrylate, hydroxypropyl methacrylate, methyl vinyl ether, alkyl vinyl ether, vinyl alcohol, methacrylic acid, acrylic acid, acrylamide, N-alkyl acrylamide, hydroxypropylmethacrylamide, vinyl acetate, 2-sulfoethyl methacrylate, 3-sulfopropyl acrylate, 3-sulfopropyl methacrylate, and PEG-methacrylate. Some exemplary substituents bearing a charge can be, for example, choline, phosphoryl choline, 2-aminoethyl methacrylate hydrochloride, N-(3-aminopropyl)methacrylamide hydrochloride, 2-N-morpholinoethyl methacrylate, vinylbenzoic acid, vinyl sulfonic acid, and styrene sulfonates.

The monomers for strength generally account for about 60 mole % to about 90 mole % of the total monomers forming the polymer, the monomers for flexibility generally account for about 0 mole % to about 40 mole % of the total monomers forming the polymer, and the hydrophilic monomers for enhancing permeability generally account for about 0 mole % to about 20 mole % of the total monomers forming the polymer. By varying the mole percentages of the three components of the polymer, one can fine-tune physical properties of the polymer.

In some embodiments, the polymer of formula I has a structure of formula II or formula III:

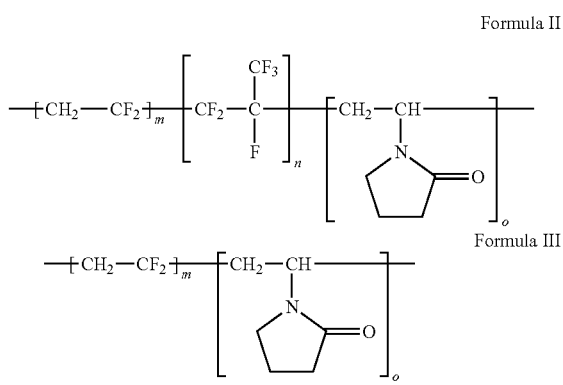

The vinyl pyrrolidone is known to be miscible with the vinylidene fluoride as both have strong dipolar interactions. Therefore, there is not a large driving force for phase separation. The vinylidene fluoride has a propensity to crystallize and, therefore provides the strength for the polymer. This strength can be tuned by the amount of hexafluoropropene, which lowers the crystallinity and promotes the flexibility of the polymer. The pyrrolidone is a hydrophilic monomer and will increase the water absorption of the polymer. Water absorption of the polymer strongly influences the drug permeability of the polymer. For example, poly(vinylidene fluoride-co-hexafluoropropene) has a very low water absorption of <0.04 w %, and it has a low drug permeability. Addition of small amounts of vinyl pyrrolidone in the range between about 1 mole % to about 10 mole % will appreciably alter drug permeability of the polymer.

In formula III, the pyrrolidone would inhibit the crystallization of the vinylidene fluoride monomers, which will increase the flexibility of the polymer. The pyrrolidone group would also impart hydrophilicity to the polymer, thereby increasing drug permeability of the polymer.

In another embodiment, the polymer of formula I has a structure of formula IV:

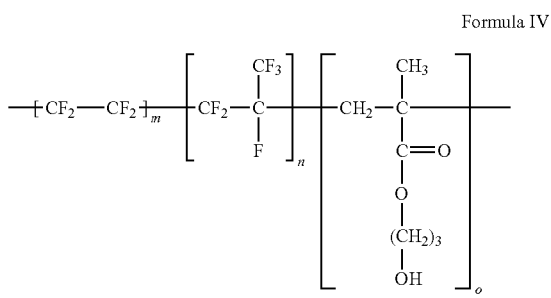

In this polymer, the tetrafluoroethylene monomer imparts strength to the polymer, and the hexafluoropropene monomer provides flexibility to the polymer. The hydrophilicity of the polymer can be tuned by the amount of 3-hydroxypropyl methacrylate. In addition, with an adequate amount of 3-hydroxypropyl methacrylate, in the range of 5-25 mole %, incorporated in to a terpolymer with 5-15 mole % hexafluoropropene, this polymer can be made solvent soluble.

The polymers described herein can be synthesized by methods known in the art (see, for example, D. Braun, et al., Polymer Synthesis: Theory and Practice. Fundamentals, Methods, Experiments. $3^{rd}$ Ed., Springer, 2001; Hans R. Kricheldorf, Handbook of Polymer Synthesis, Marcel Dekker Inc., 1992; G. Odian, Principles of Polymerization, $3^{rd}$ ed. John Wiley & Sons, 1991). For example, one method that can be used to make the polymer can be free radical methods (see, for example, D. Braun, et al., Polymer Synthesis: Theory and Practice. Fundamentals, Methods, Experiments. $3^{rd}$ Ed., Springer, 2001; Hans R. Kricheldorf, Handbook of Polymer Synthesis, Marcel Dekker Inc., 1992). Polymerization by suspension or emulsion techniques utilizing free radical initiation is commonly employed. Block copolymers and terpolymers can be produced by atom transfer polymerization. Grafting of hydrophilic monomers onto pre-made poly(vinylidene fluoride-co-hexafluoropropylene) can be accomplished by ozonation of the fluoropolymer followed by thermally induced graft polymerization of the hydrophilic monomer. Polymerization in solvent can also be used to synthesize the polymers described herein.

Polymer Blends

In another embodiment, a hydrophobic polymer of fluorinated monomers such as polyvinylidene fluoride (PDVF) or poly(vinylidene fluoride-co-hexafluoropropylene) (PVDF-co-HFP) can be blended with one or more additional biocompatible polymers having different hydrophilicity and/or flexibility to generate a polymer blend coating material that has desired flexibility and drug permeability. Generally, useful polymers that can be blended with the polymer of fluorinated monomers are substantially miscible with the polymer of fluorinated monomers. In a further embodiment, any of the polymers of formulae I-IV can be blended with one or more additional biocompatible polymer, which is described below.

The additional biocompatible polymer can be biodegradable (both bioerodable or bioabsorbable) or nondegradable, and can be hydrophilic or hydrophobic. Hydrophilic is defined to have a δ value greater than about 8.5, e.g., a δ value of about 8.5, about 9.5, about 10.5 or about 11.5.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly polyesters, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. PEO/PLA); polyalkylene oxides such as poly(ethylene oxide), or poly(propylene oxide); poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and N-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, and combinations thereof. In some embodiments, the polymer can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), and poly(L-lactic acid-co-glycolic acid), respectively.

Biobeneficial Material

The copolymer of fluorinated monomers and hydrophilic monomers can form a coating optionally with a biobeneficial material. The combination can be mixed, blended, or coated in separate layers. The biobeneficial material useful in the coatings described herein can be a polymeric material or non-polymeric material. The biobeneficial material is preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly(ether-esters) (e.g. PEO/PLA); polyalkylene oxides such as poly(ethylene oxide), or poly(propylene oxide)); poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), polystyrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block-poly(ethylene glycol)) (PEG-PBT-PEG).

In a preferred embodiment, the biobeneficial material can be a polyether such as poly(ethylene glycol) (PEG) or polyalkylene oxide.

Bioactive Agents

The polymeric coatings or the polymeric substrate described herein may optionally include one or more bioactive agents. These bioactive agents can be any agent which is a therapeutic, prophylactic, or diagnostic agent. These agents can have anti-proliferative or anti-inflammmatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable-therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antiproliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-

[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device itself, such as a stent, can also be made from the described inventive polymers or polymer blends.

Method of Use

In accordance with embodiments of the invention, a coating of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth prophetic examples. All parameters and data are not to be construed to unduly limit the scope of the embodiments of the invention.

Example 1

Synthesis of poly(vinylidene fluoride-co-hexafluoropropylene-co-vinyl pyrrolidone), 80/15/5 molar ratio A 20 gallon glass lined autoclave is filled with 11 gallons of deionized water, and then sparged with nitrogen to remove oxygen. The autoclaved is then charged with 3.47 kg of vinylidene fluoride (VDF) and 1.53 Kg of hexafluoropropylene (HFP). 40 g of a 70% solution of tertiary butyl hydroperoxide in water is diluted to 250 ml with deionized water. 31 g of sodium metabisulfite and 6.3 g of ferrous sulfate heptahydrate is diluted to 250 ml with deionized water. These two solutions are added separately to the autoclave over a ten period time period. The autoclave is maintained throughout the entire polymerization between 15-25° C. After 30 minutes into the polymerization, vinyl pyrrolidone is pumped into the autoclave. After consumption of the initial charge of VDF and HFP, VDF and HFP are added to the autoclave at the stoichiometric ratio to maintain a reactor pressure of 50-130 psig. In total, 25 kg of VDF, 11 kg of HFP, and 2.7 kg of vinyl pyrrolidone is added to the autoclave. After consumption of all monomers, the autoclave is vented, and the water removed. The polymer is purified by extracting twice with 20 liters of methanol followed by drying in vacuo.

Example 2

Synthesis of poly(vinylidene fluoride-co-hexafluoropropene-co-vinyl pyrrolidone), molar ratio 80/18/2 by atom transfer polymerization To a 2.5 gallon stainless steel autoclave equipped with agitation is added copper bromide (28 g, 0.195 mole), 2,2'-bipyridine (60.9 g, 0.39 mole), and 1,2-diiodoethane (55 g, 0.195 mole). The autoclave is purged with argon to remove all oxygen. $CO_2$ is introduced to reach a pressure of 1200 psig and the autoclave thermostated to ambient temperature. The autoclave is then charged with 1 kg of VDF and 528 g of HFP. The temperature is raised to 40° C. and the reaction allowed to proceed for 20 hours. Vinyl pyrrolidone is added (43.4 g) and the polymerization allowed to proceed for 11 more hours. After venting the autoclave the polymer is dissolved in 5 liters of acetone and then isolated by precipitation into methanol.

Example 3

Preparation of a Drug Eluting Stent Coating Using the Polymer of Example 1

A polymer solution containing between about 0.1 mass % and about 15 mass %, for example, about 2.0 mass % of PBMA and the balance, a solvent mixture of acetone and cyclohexanone, the solvent mixture containing about 60 mass % of acetone and about 40 mass % of xylene is prepared. The solution is applied onto a stent to form a primer layer. To apply the primer layer, a spray apparatus, such as an EFD 780S spray nozzle with a VALVEMATE 7040 control system (manufactured by EFD, Inc. of East Providence, R.I.) can be used. The EFD 780S spray nozzle is an air-assisted external mixing atomizer. The composition is atomized by air and applied to the stent surfaces. During the process of applying the composition, the stent can be optionally rotated about its longitudinal axis, at a speed of 50 to about 150 rpm. The stent can also be linearly moved along the same axis during the application.

The poly(butyl methacrylate) (PBMA) solution can be applied to a 12-mm small VISION stent (available from Guidant Corporation) in a series of 10-second passes, to deposit, for example, 10 µg of coating per spray pass. Between the spray passes, the stent is dried for about 10 seconds using flowing air with a temperature of about 60° C. Five spray passes can be applied, followed by baking the primer layer at about 80° C. for about 1 hour. As a result, a primer layer can be formed having a solids content of about 50 µg. "Solids" means the amount of the dry residue deposited on the stent after all volatile organic compounds (e.g., the solvent) have been removed.

A drug-containing formulation can be prepared containing:

(a) between about 0.1 mass % and about 15 mass %, for example, about 2.0 mass % of the polymer of example 1;

(b) between about 0.1 mass % and about 2 mass %, for example, about 0.8 mass % of an active agent, for example, everolimus; and (c) the balance, a solvent mixture of acetone, the solvent mixture containing about 70 mass % of acetone and about 30 mass % of cyclohexanone.

In a manner identical to the application of the primer layer, nineteen spray passes is performed, followed by baking the drug-polymer layer at about 50° C. for about 2 hours, to form the drug-polymer reservoir layer having a solids content between about 30 µg and 750 µg, for example, about 190 µg, and a drug content of between about 10 µg and about 250 µg, for example, 50 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable device having a coating thereon, wherein the coating comprises a biocompatible copolymer comprising fluorinated monomers and hydrophilic monomers, wherein the copolymer has a structure of formula I:

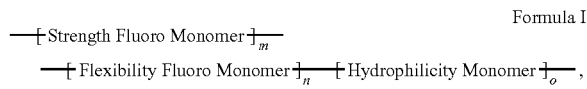

Formula I and m, n and o are integers and all above zero, wherein the copolymer is generated by direct polymerization of the fluorinated monomers and the hydrophilic monomers.

2. The implantable device of claim 1, wherein the strength fluoro monomer is selected from the group consisting of $-CF_2-CF_2-$, $-CH_2-CF_2-$, $-CH_2-CHF-$, $-CF_2-CHF-$, $-CHF-CHF-$, or $-CF_2-CRF-$ where R can be phenyl, cyclic alkyl, heterocyclic, heteroaryl, fluorinated phenyl, fluorinated cyclic alkyl, or fluorinated heterocyclic, wherein the flexibility fluoro monomer is selected from substituted fluorinated ethylene monomers that bear a substituent, wherein the hydrophilic monomer is selected from the group consisting of vinyl monomers that bear a pyrrolidone group(s), carboxylic acid group(s), sulfonic acid group(s), sulfone group(s), amino group(s), alkoxy group(s), amide group(s), ester group(s), acetate group(s), poly(ethylene glycol) group(s), poly(propylene glycol) group(s), poly(tetramethylene glycol) group(s), poly(alkylene oxide) group(s), hydroxyl group(s), or a substituent that contains a charge or one of pyrrolidone group(s), carboxylic acid group(s), sulfone group(s), sulfonic acid group(s), amino group(s), alkoxy group(s), amide group(s), ester group(s), acetate group(s), poly(ethylene glycol) group(s), poly(propylene glycol) group(s), poly(tetramethylene glycol) group(s), poly(alkylene oxide) group(s), hydroxyl group(s), and combinations thereof.

3. The implantable device of claim 2, wherein the flexibility monomer can be —$CF_2$—CRF—, —CHF—CRF—, and —$CF_2$—CRH—, or combinations thereof in which R is selected from the group consisting of trifluoromethyl, F, Cl, Br, I, short chain alkyl groups from $C_2$ to $C_{12}$, fluorinated short chain alkyl groups from $C_2$ to $C_{12}$, and combinations thereof.

4. The implantable device of claim 1, wherein the hydrophilic monomer is selected from the group consisting of vinyl pyrrolidone, hydroxyethyl methacrylate, hydroxypropyl methacrylate, methyl vinyl ether, alkyl vinyl ether, vinyl alcohol, methacrylic acid, acrylic acid, acrylamide, N-alkyl acrylamide, hydroxypropylmethacrylamide, vinyl acetate, 2-sulfoethyl methacrylate, 3-sulfopropyl acrylate, 3-sulfopropyl methacrylate, PEG-methacrylate, 2-aminoethyl methacrylate hydrochloride, N-(3-aminopropyl)methacrylamide hydrochloride, 2-N-morpholinoethyl methacrylate, vinylbenzoic acid, vinyl sulfonic acid, styrene sulfonates, a monomer that bears a charge, and combinations thereof.

5. The implantable device of claim 2, wherein the hydrophilicity monomer is selected from the group consisting of vinyl pyrrolidone, hydroxyethyl methacrylate, hydroxypropyl methacrylate, methyl vinyl ether, alkyl vinyl ether, vinyl alcohol, methacrylic acid, acrylic acid, acrylamide, N-alkyl acrylamide, hydroxypropylmethacrylamide, vinyl acetate, 2-sulfoethyl methacrylate, 3-sulfopropyl acrylate, 3-sulfopropyl methacrylate, PEG-methacrylate, 2-aminoethyl methacrylate hydrochloride, N-(3-aminopropyl)methacrylamide hydrochloride, 2-N-morpholinoethyl methacrylate, vinylbenzoic acid, vinyl sulfonic acid, styrene sulfonates, a monomer that bears a charge, and combinations thereof.

6. The implantable device of claim 1, wherein the biocompatible polymer has a structure of any of formula II and Formula IV:

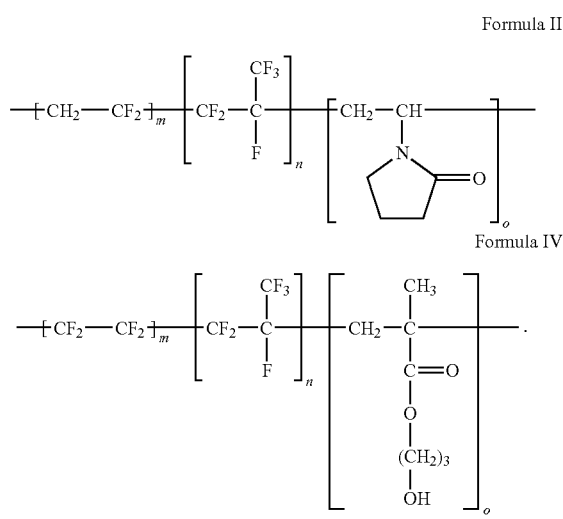

7. The implantable device of claim 2, wherein the strength fluoro monomer is in the range from about 60 mole % to about 90 mole %, wherein the flexibility fluoro monomer is in the range from above 0 mole % to about 40 mole %, and wherein the hydrophilic monomer is in the range from above 0 mole % to about 20 mole %.

8. The implantable device of claim 1, further comprising a bioactive agent.

9. The implantable device of claim 8, wherein the bioactive agent is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and a combination thereof.

10. The implantable device of claim 1, which is a stent.

11. The implantable device of claim 8, which is a stent.

12. The implantable device of claim 9, which is a stent.

* * * * *